United States Patent [19]

Lindahl, III et al.

[11] 4,411,839
[45] Oct. 25, 1983

[54] α-CYANO-β-(TRISUBSTITUTED PHENYLHYDRAZINO)-N-ETHOXYCARBONYLACRYLAMIDES

[75] Inventors: George R. Lindahl, III, Mountain View; Clive A. Henrick, Palo Alto, both of Calif.

[73] Assignee: Zoecon Corporation, Palo Alto, Calif.

[21] Appl. No.: 382,527

[22] Filed: May 27, 1982

Related U.S. Application Data

[63] Continuation of Ser. No. 187,001, Sep. 15, 1980, abandoned.

[51] Int. Cl.$^3$ ............................................. C07C 121/78
[52] U.S. Cl. ................................ 260/465 D; 544/311; 544/312; 71/92
[58] Field of Search ...................................... 260/465 D

[56] References Cited

U.S. PATENT DOCUMENTS 2,965,643  12/1960  Druey et al. ..................... 544/262
4,266,056  5/1981   Hendrick et al. ................. 544/311

OTHER PUBLICATIONS

Shaw, *J. Chem. Soc.*, 1955, 1834–1840.
Lees et al., *J. Chem. Soc.(C)*, 1968, 1519–1521.
Farmaco Ed. Sci. 22(1967), pp. 58–75 & 418.

*Primary Examiner*—Paul M. Coughlan, Jr.

[57]        ABSTRACT

Novel 1-substituted pyrimidinediones and thiopyrimidineones, synthesis thereof and intermediates therefor, useful as control agents for pests.

2 Claims, No Drawings

α-CYANO-β-(TRISUBSTITUTED PHENYLHYDRAZINO)-N-ETHOXYCARBONYLA-CRYLAMIDES

This is a continuation of application Ser. No. 187,001, filed Sept. 15, 1980, now abandoned.

This invention relates to novel 1-substituted pyrimidinediones and thiopyrimidinenones, synthesis thereof and intermediates therefor, useful as control agents for pests, most notably as fungicides and herbicides.

The compounds of the present invention are represented by the following formula A:

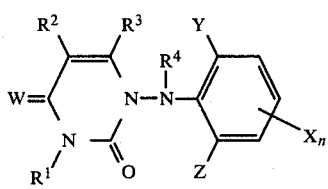
(A)

wherein,
$R^1$ is hydrogen, lower alkyl, lower alkylthio, lower haloalkylthio, or lower hydroxyalkyl;
$R^2$ is hydrogen, cyano, bromo, chloro, fluoro, carboxyl or lower alkylcarboxyl;
$R^3$ is hydrogen, lower alkyl, cyano, bromo, chloro, fluoro or amino;
$R^4$ is independently selected from the values of $R^1$;
W is oxygen or sulfur;
X is lower alkyl, lower alkoxy, bromo, chloro, fluoro, lower haloalkyl, nitro, lower alkylthio, lower alkylcarbonyl or lower haloalkoxy;
Y is hydrogen or independently selected from the values of X;
Z is hydrogen or independently selected from the values of X; and
n is zero, one, two or three;
provided that when W is oxygen, $R^2$ is cyano, each of $R^1$, $R^3$ and $R^4$ is hydrogen and n is zero—then at least one of Y and Z is other than hydrogen.

The synthesis of the compounds of formula A' (W is oxygen, $R^1$ is hydrogen, $R^2$ is cyano) can be outlined as follows:

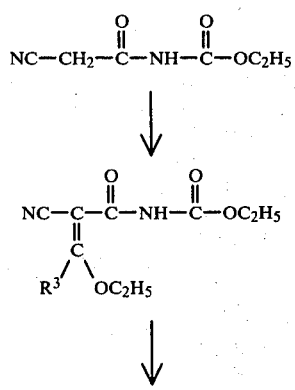

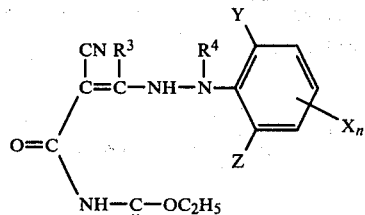
(III)

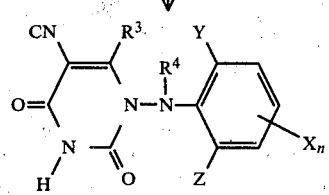
(A')

In the practice of the above synthesis, N-ethoxycarbonylcyanoacetamide (I) is reacted, for example, with triethyl orthoformate in acetic anhydride to prepare α-cyano-β-ethoxy-N-ethoxycarbonylacrylamide (II, $R^3$ is hydrogen). The use of triethyl orthoacetate and triethyl orthopropionate in place of triethyl orthoformate gives II wherein $R^3$ is methyl and ethyl, respectively. II, in ethanol, is heated with a substituted hydrazine (II') to obtain the β-substituted hydrazino compound III.

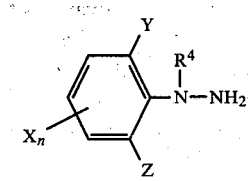
(II')

III is cyclized on heating in a high boiling solvent, preferably a solvent in which III is soluble, such as p-cymene, tetralin, ortho-dichlorobenzene and the like, to yield the 1-anilino-5-cyanopyrimidinedione (A'). Each step of the above outlined synthesis proceeds in essentially quantitative yield with II, III and A in the form of solids convenient to separate by filtration. The above outlined synthesis follows the synthetic route reported by G. Shaw, J. Chem. Soc., 1955, 1834 and by Senda et al., Chem. Pharm. Bull., 20(7), 1380–1388 (1972) and literature cited therein. C. F. Lees, et al., J. Chem. Soc. (C), 1519 (1968); Senda et al., J. Org. Chem., 40(3), 353 (1975); and Offenlegungsschrift 25 09 037 (1976).

The compounds of formula A wherein $R^1$ is lower alkyl are prepared by alkylation of a compound of A where $R^1$=H using, for example, dimethyl sulfate. Alternately, where $R^1$ is lower alkyl, as well as lower alkylthio or lower haloalkylthio, the sodium salt of a compound of formula A is reacted with $R^1X'$ ($X'$ is bromo, chloro or iodo) in an organic solvent such as dimethylformamide. Compouds of formula A wherein $R^1$ is lower hydroxyalkyl are made by reacting A (where $R^1$=H) with formaldehyde at high temperature and pressure.

The compounds of formula A wherein $R^2$ is lower alkylcarboxyl are prepared in the same manner as outlined previously where $R^2$ is cyano except that a compound of formula I' is used to yield a compound (A"). The other reactants and conditions are unchanged ($R^5$=lower alkyl).

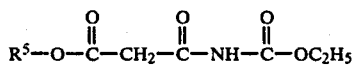
(I')

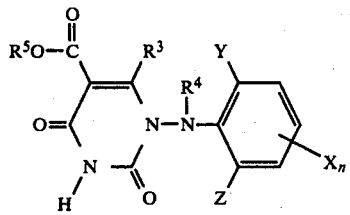
(A")

To give a compound where $R^2$ is carboxyl, a compound of formula A" is acid hydrolyzed. Such a compound where $R^2$ is carboxyl can be decarboxylated and then halogenated, reacting for example with bromine or N-chlorosuccinimide, to prepare the compounds of formula A wherein $R^2$ is bromo, chloro or fluoro.

To prepare compounds of formula A wherein $R^3$ is cyano, a compound of formula A where $R^2$ is, for example, bromo or chloro is reacted with one equivalent of a source of cyanide such as sodium cyanide in a solvent such as ethanol.

Compounds of formula A where $R^3$ is bromo or chloro are prepared by reacting cyanoacetic acid with a semicarbazide of formula (IV) and acetic anhydride at reflux temperature. The resulting compound (V) is treated with sodium hydroxide at elevated temperature to give the pyrimidinedione (VI). See Papesch, *J. Org. Chem.*, 16, 1879 (1951). Compound (VI) is reacted first with sodium nitrite in hydrochloric acid and then with CuX'(where X'=chloride or bromide) to give the pyrimidinedione (VII) where $R^3$ is chloro or bromo.

Where $R^3$ is fluoro, the same procedure is followed except that the pyrimidinedione (VI) is reacted with sodium nitrite and fluoboric acid followed by pyrolyzation to give the pyrimidinedione (VIII).

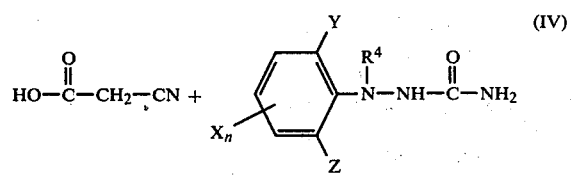
(IV)

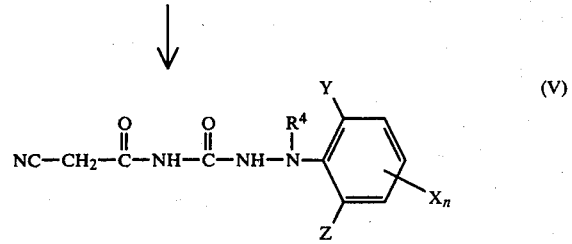
(V)

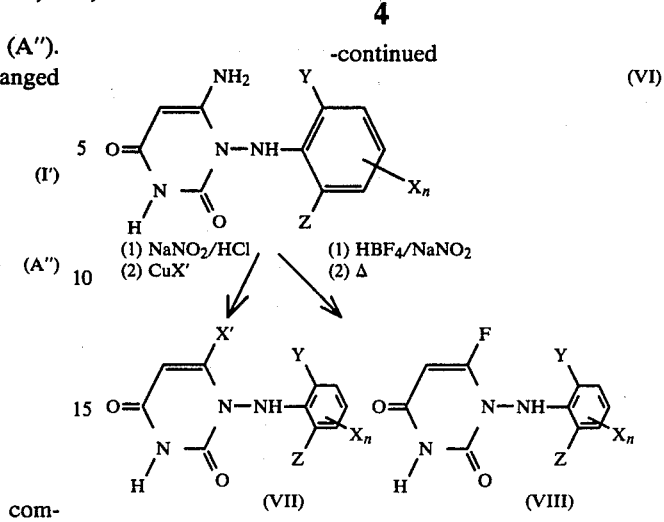

To prepare compounds of formula A where $R^4$ is lower hydroxyalkyl, a compound of A where $R^4$ is hydrogen is reacted with formaldehyde in the presence of formic acid at reflux temperature (the Eschweiler-Clarke reaction). Where $R^4$ is lower alkyl, a compound of A ($R^4$=H) is alkylated using, for example, diethyl sulfate. Where $R^4$ is lower alkylthio or lower haloalkylthio, a compound $R^4$X'(X'=bromo, chloro or iodo) is reacted with the sodium salt of a compound of formula A in an organic solvent such as tetrahydrofuran or dimethylformamide.

To prepare the 4-thiopyrimid-2-ones of formula A, a compound of A where W is oxygen is reacted with phosphorus pentasulfide and pyridine with heating at reflux to yield the corresponding compound where W is sulfur. See McElvain et al., *J. Am. Chem. Soc.*, 73, 1988 (1951); and Arutyanyun et al., CA 73:77184C.

The term "lower alkyl," as used herein, refers to a lower alkyl group of one to six carbon atoms. The term "lower alkoxy," as used herein, refers to a lower alkoxy group of one to six carbon atoms. The term "lower alkylthio," as used herein, refers to a lower alkylthio group of one to six carbon atoms. The term "lower haloalkyl," as used herein, refers to a lower alkyl group substituted with one to three atoms of bromine, chlorine or fluorine. The term "lower haloalkoxy," as used herein, refers to a lower alkoxy group substituted with one to three atoms of bromine, chlorine or fluorine. The term "lower haloalkylthio," as used herein, refers to a lower alkylcarbonyl group of two to seven carbon atoms. The term "lower haloalkylthio," as used herein, refers to a lower alkylthio group substituted with one to three atoms of bromine, chlorine or fluorine. The term "lower alkylcarboxyl," as used herein, refers to a lower alkylcarboxyl group of two to seven carbon atoms. The term "lower hydroxyalkyl," as used herein, refers to a lower hydroxyalkyl group of one to six carbon atoms.

The compounds of the present invention are useful as herbicides. These compounds appear to be selective in their activities—while some of the compounds embraced by the present invention are active herbicides against broad-leaved plants, other compounds of this invention show herbicidal activity against grasses. Some examples of plants against which the compounds of the present invention are useful herbicides are broadleaf plants such as Ipomoea sp. (morning glory), Sesbania sp. (sesbania), *Datura stramonium* (jimsonweed), and Solanum sp. (nightshade) and grasses such as *Seta-*

*ria viridis* (green foxtail), *Avena fatua* (wild oats) and *Sorghum bicolor* (shattercane). The compounds of formula A can generally be used systemically by application to the soil or topically by application directly to the target plant following conventional methods. The compounds of the present invention are solids which may be formulated in suitable solid or liquid carriers in a conventional way for herbicidal formulations. The compounds of the present invention are usually applied at a concentration of from about 0.5 lb. per acre to about 10 lb. per acre.

The compounds of the present invention may be used in combination with other herbicides such as, for example, N-(phosphonomethyl)glycine; 3-amino-s-triazole; 2-[4-(2,4-dichlorophenoxy)-phenoxy]propanoic acid; 3′,4′-dichloropropionanilide; isopropyl m-chlorocarbanilate; $\alpha,\alpha,\alpha$-trifluoro-2,6-dinitro-N,N-dipropyl-p-toluidine; 1,1′-dimethyl-4,4′-bipyridinium ion; 2-chloro-4-(ethylamino)-6-(isopropylamino)-s-triazole; (2,4-dichlorophenoxy)-acetic acid; 5-bromo-3-sec-butyl-6-methyluracil; 2-sec-butyl-4,6-dinitrophenol; 3-(3,4-dichlorophenyl)-1-methoxy-1-methylurea; and 2-chloro-1-(3-ethoxy-4-nitrophenoxy)-4-(trifluoromethyl)benzene.

The compounds of formula A are also useful biological agents against plant pathogens. More particularly, the compounds of the present invention are useful fungicides and bacteriocides for the control of pathogenic diseases of plants. For example, during periods of adverse climactic conditions such as excess and prolonged moisture and mild to cool temperatures, many plants such as rice, tomato, peppers and cabbage and fruits are susceptible to and damaged by fungal and bacterial diseases caused by microorganisms belonging to Piricularia, Xanthomonas, Erwinia, and the like, such as the species *Piricularia oryzae, Xanthomonas oryzae* or *Erwinia amylovora*. The compounds of the present invention are useful in combating such diseases. The compounds of the present invention can generally be used either systemically or topically by conventional application methods. The compounds of the present invention are solids which may be formulated in suitable solid or liquid carriers in a conventional way for plant fungicidal or bacteriocidal formulations. The compounds of the present invention are usually applied at a concentration of from about 0.01 to 10.0 percent, by weight, or higher.

The compounds of the present invention can be used as industrial (as opposed to agricultural) bactericides and fungicides, e.g. as paint film fungicides. The compounds also have plant growth regulating properties.

The compounds of the present invention may be used in combination with other compound(s) having biological activity [e.g., other growth stimulating substances such as the gibberellins (e.g., $GA_3$, $GA_4$ or $GA_7$), the auxins (e.g., indoleacetic or indolebutyric acid), and the cytokinins (e.g., kinetin, diphenylurea, benzimidazole and benzyladenine), and other compounds having complementary fungicidal or insecticidal activity].

Suitable solid carriers include talc, kaolin, silica, and diatomaceous earth to which may be added wetting agents, dispersing agents, and the like, to form wettable powders. The wettable powder can be diluted with water to the desired concentration and applied to the soil and/or plant surface.

The active ingredients may be used as such, for example for fungicidal or herbicidal purposes, but are more conveniently formulated into compositions for such usage.

The active ingredients of the compositions, and salts thereof, can be applied in a number of ways, depending on their use, for example they can be applied, formulated or unformulated, directly to the foliage of a plant, or they can be applied to bushes and trees, to seeds or to other medium in which plants, bushes or trees are growing or are to be planted, or they can be sprayed on, dusted on or applied as a cream or paste formulation.

The compositions may be in the form of dusting powders or granules comprising the active ingredient and a solid diluent or carrier, for example kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example, a mineral oil) for assisting the adhesion of the composition to the seed. Alternatively, the active ingredient can be formulated for seed dressing purposes using an organic solvent (for example, N-methylpyrrolidone or dimethylformamide).

The compositions may also be in the form of dispersible powders, granules or grains comprising a wetting agent to facilitate their dispersion in liquids. The powders, granules or grains may also contain fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are acetone, acetic acid, dimethylsulfoxide and dimethylformamide.

The compositions to be used as sprays may also be in the form of aerosols wherein the formulation is held in a container under pressure in the presence of a propellant, e.g., fluorotrichloromethane or dichlorodifluoromethane.

The active ingredients can be mixed in the dry state with a pyrotechnic mixture to form a composition suitable for generating in enclosed spaces a smoke containing the compounds.

Alternatively, the active ingredients may be used in a microencapsulated form.

By including suitable additives, for example additives for improving the distribution, adhesive power and resistance to rain on treated surfaces, the different compositions can be better adapted for various utilities.

The active ingredients can be used as mixtures with fertilizers (e.g., nitrogen-, potassium- or phosphorus-containing fertilizers). Compositions comprising only granules of fertilizer incorporating, for example coated with, a compound of formula A are preferred. Such granules suitably contain up to 25% by weight of the compound.

The following examples are provided to illustrate the practice of the present invention. RT means room temperature. Temperature is given in degrees Centigrade.

EXAMPLE 1

A mixture of N-ethoxycarbonylcyanoacetamide (42 g), triethylorthoformate (40 g) and acetic anhydride (100 ml) is heated at reflux for one hour. The reaction is allowed to stand until cool and then is filtered, washing with ether, to yield $\alpha$-cyano-$\beta$-ethoxy-N-ethoxycarbonylacrylamide.

Four grams (18.9 mmol) of α-cyano-β-ethoxy-N-ethoxycarbonylacrylamide is dissolved in hot ethanol/toluene. To this is added, portionwise, 4 g of 2,4,6-trichlorophenylhydrazine. The mixture is heated to reflux for three days. Cooling of the mixture and evaporation of the solvent gives the crude product, which is recrystallized from ethanol (3 X) to yield α-cyano-β-(2,4,6-trichlorophenylhydrazino)-N-ethoxycarbonylacrylamide, m.p. =161° (dec.).

To 7 ml of tetralin is added 1.5 g of α-cyano-β-(2,4,6-trichlorophenylhydrazino)-N-ethoxycarbonylacrylamide, and this mixture is heated to 180°–200° under nitrogen for 30 minutes. After cooling, the resulting solid is filtered, washed with pentane, slurried with acetone/hexane and again filtered to give 1-(2,4,6-trichloroanilino)-5-cyano-2,4-pyrimidinedione, m.p.>320°.

EXAMPLE 2

Following the procedure of Example 1, each of 4-chlorophenylhydrazine, 2-methoxy-phenylhydrazine, 2,5-dichlorophenylhydrazine, 2-methylphenylhydrazine, 2,6-dinitro-4-trifluoromethylphenylhydrazine, 2-methylthiophenylhydrazine, 6-chloro-4-ethoxy-2-methylphenylhydrazine, 4-difluoromethoxyphenylhydrazine and 2,3,4,5,6-pentafluorophenylhydrazine is reacted with α-cyano-β-ethoxy-N-ethoxycarbonylacrylamide to give the corresponding compound in column I.

I

α-cyano-β-(4-chlorophenylhydrazino)-N-ethoxycarbonylacrylamide, m.p.=134° (dec)
α-cyano-β-(2-methoxyphenylhydrazino)-N-ethoxycarbonylacrylamide, m.p.=151°–152°
α-cyano-β-(2,5-dichlorophenylhydrazino)-N-ethoxycarbonylacrylamide, m.p.=118° (dec)
α-cyano-β-(2-methylphenylhydrazino)-N-ethoxycarbonylacrylamide, m.p.=163.5°–165°
α-cyano-β-(2,6-dinitro-4-trifluoromethylphenylhydrazino)-N-ethoxycarbonylacrylamide, m.p.=196°–198° (dec)
α-cyano-β-(2-methylthiophenylhydrazino)-N-ethoxycarbonylacrylamide
α-cyano-β-(6-chloro-4-ethoxy-2-methylphenylhydrazino)-N-ethoxycarbonylacrylamide
α-cyano-β-(4-difluoromethoxyphenylhydrazino)-N-ethoxycarbonylacrylamide
α-cyano-β-(2,3,4,5,6-pentafluorophenylhydrazino)-N-ethoxycarbonylacrylamide, m.p.=144°–146°
Each of the products in column I is cyclized to give

II 5-cyano-1-(4-chloroanilino)-2,4-pyrimidinedione, m.p.=>300°
5-cyano-1-(2-methoxyanilino)-2,4-pyrimidinedione, m.p.=310°–311° (dec)
5-cyano-1-(2,5-dichloroanilino)-2,4-pyrimidinedione, m.p.=>305°
5-cyano-1-(2-methylanilino)-2,4-pyrimidinedione, m.p.=265°–267°
5-cyano-1-(2,6-dinitro-4-trifluoromethylanilino)2,4-pyrimidinedione, m.p.=>305°
5-cyano-1-(2-methylthioanilino)-2,4-pyrimidinedione
5-cyano-1-(6-chloro-4-ethoxy-2-methylanilino)-2,4-pyrimidinedione
5-cyano-1-(4-difluoromethoxyanilino)-2,4-pyrimidinedione 5-cyano-1-(2,3,4,5,6-pentafluoroanilino)-2,4-pyrimidinedione, m.p.=>320°.

Example 3

5-Cyano-1-(2,4,6-trichloroanilino)-2,4-pyrimidinedione (0.8 g, 3 mmol) is dissolved in 8 ml of 1 N sodium hydroxide followed by the dropwise addition of 0.8 ml (8.4 mmol) of dimethyl sulfate, with stirring at RT. The product is filtered, washed with water and dried to give 5-cyano-3-methyl-1-(2,4,6-trichloro-N-methylanilino)-2,4-pyrimidinedione, m.p.=175°–178°.

EXAMPLE 4

Two grams of 5-cyano-1-(2,4,6-trichloroanilino)-2,4-pyrimidinedione is added to 1.6 ml of 35% formaldehyde in enough 95% formic acid to effect stirring. The mixture is heated to reflux and 95% formic acid is added dropwise until the solid is dissolved. The mixture is refluxed overnight, after which 3.2 ml of aqueous formaldehyde is added and refluxing is continued for another 8 hours. The reaction mixture is poured into water and the precipitate is filtered to yield the compound 5-cyano-1-(N-hydroxymethyl-2,4,6-trichloroanilino)-2,4-pyrimidinedione, m.p.>300°.

EXAMPLE 5

Following the method of Example 1, N-ethoxycarbonylcyanoacetamide is heated with triethyl orthoacetate and acetic anhydride to give α-cyano-β-ethoxy-β-methyl-N-ethoxycarbonylacrylamide, which in turn is reacted with 2,4,6-trichlorophenylhydrazine. The resulting compound α-cyano-β-methyl-β-(2,4,6-trichlorophenylhydrazino)-N-ethoxycarbonylacrylamide (m.p.=183°–184°) is cyclized, yielding 5-cyano-6-methyl-1-(2,4,6-trichloroanilino)-2,4-pyrimidinedione, m.p.=>305°.

In the same manner, 5-cyano-6-ethyl-1-(2-methylanilino)-2,4-pyrimidinedione is made by using triethyl orthopropionate rather than triethyl orthoacetate to give α-cyano-β-ethoxy-β-ethyl-N-ethoxycarbonylacrylamide, which is reacted with 2-methylphenylhydrazine, followed by cyclization.

EXAMPLE 6

Each of the compounds listed in column III is reacted with α-cyano-β-ethoxy-N-ethoxy-carbonylacrylamide, following the procedure of Example 1, and the resulting product is cyclized by heating in tetralin to yield the pyrimidinedione listed in column IV.

III 2,6-dimethylphenylhydrazine
4-isopropylphenylhydrazine
4-bromo-2-fluorophenylhydrazine
2,6-dimethyl-4-methoxyphenylhydrazine
3-chloro-2,6-dimethylphenylhydrazine
2,6-dichlorophenylhydrazine
2-methyl-6-methylthiophenylhydrazine
4-fluoro-2-methylphenylhydrazine
4-trifluoromethylphenylhydrazine
3-n-butylphenylhydrazine
2-chloro-6-methylphenylhydrazine
4-acetylphenylhydrazine
2-ethyl-4-methylphenylhydrazine

IV 5-cyano-1-(2,6-dimethylanilino)-2,4-pyrimidinedione
5-cyano-1-(4-isopropylanilino)-2,4-pyrimidinedione 5-cyano-1-(4-bromo-2-fluoroanilino)-2,4-pyrimidinedione 5-cyano-1-(2,6-dimethyl-4-methoxyanilino)-2,4-pyrimidinedione 5-cyano-1-(3-chloro-2,6-dimethylanilino)-2,4-pyrimidinedione 5-cyano-1-(2,6-dichloroanilino)-2,4-pyrimidinedione, m.p.=>320°

5-cyano-1-(2-methyl-6-methylthioanilino)-2,4-pyrimidinedione 5-cyano-1-(4-fluoro-2-methylanilino)-2,4-pyrimidinedione 5-cyano-1-(4-trifluoromethylanilino)-2,4-pyrimidinedione 5-cyano-1-(3-n-butylanilino)-2,4-pyrimidinedione 5-cyano-1-(2-chloro-6-methylanilino)-2,4-pyrimidinedione 5-cyano-1-(4-acetylanilino)-2,4-pyrimidinedione 5-cyano-1-(2-ethyl-4-methylanilino)-2,4-pyrimidinedione

EXAMPLE 7

To a mixture of 5-cyano-1-(2,6-dimethylanilino)-2,4-pyrimidinedione (0.1 mol) and 80 ml of 5% sodium hydroxide solution, with stirring, is slowly added dimethyl sulfate (0.1 mol). The reaction mixture is stirred for about 2-4 hours and then filtered, washed with water and dried to yield 5-cyano-1-(2,6-dimethylanilino)-3-methyl-2,4-pyrimidinedione.

Following the above procedure, 5-cyano-3,6-dimethyl-1-(2,6-dimethylanilino)-2,4-pyrimidinedione is prepared from 5-cyano-1-(2,6-dimethylanilino)-6-methyl-2,4-pyrimidinedione. 5-Cyano-1-(2,6-dimethylanilino)-6-methyl-2,4-pyrimidinedione is made from α-cyano-β-ethoxy-β-methyl-N-ethoxycarbonylacrylamide and 2,6-dimethylphenylhydrazine following the method of Example 5.

EXAMPLE 8

Following the procedure of Example 1, α-cyano-β-ethoxy-N-ethoxycarbonylacrylamide is reacted with phenylhydrazine to give α-cyano-β-phenylhydrazino-N-ethoxycarbonylacrylamide, which in turn is cyclized by heating in tetralin, yielding 5-cyano-1-anilino-2,4-pyrimidinedione. The foregoing compound has been reported by G. Shaw, *J. Chem. Soc.*, 1955, 1834–1840.

EXAMPLE 9

Following the procedure of Example 1, α-cyano-β-ethoxy-N-ethoxycarbonylacrylamide is reacted with each of 2-chlorophenylhydrazine, 2,3-dimethylphenylhydrazine and 3-methoxy-2-methylphenylhydrazine to give, respectively, α-cyano-β-(2-chlorophenylhydrazino)-N-ethoxycarbonylacrylamide, α-cyano-β-(2,3-dimethylphenylhydrazino)-N-ethoxycarbonylacrylamide and α-cyano-β-(3-methoxy-2-methylphenylhydrazino)-N-ethoxycarbonylacrylamide, each of which is cyclized to yield 5-cyano-1-(2-chloroanilino)-2,4-pyrimidinedione, 5-cyano-1-(2,3-dimethylanilino)-2,4-pyrimidinedione, and 5-cyano-1-(3-methoxy-2-methylanilino)-2,4-pyrimidinedione.

EXAMPLE 10

To 2 g of α-cyano-β-ethoxy-N-ethoxycarbonylacrylamide, dissolved in hot ethanol/toluene, and 1 ml of acetic acid is added 2 g of 2,46-trichlorophenylhydrazine. This mixture is heated to reflux for 2 to 3 hours. Cooling, evaporation of the solvent and recrystallization from acetic acid yield α-cyano-β-(2,4-trichlorophenylhydrazino)-N-ethoxycarbonylacrylamide. This compound is cyclized by heating in tetralin to give 5-cyano-1-(2,4,6-trichloroanilino)-2,4-pyrimidinedione.

A mixture of 5-cyano-1-(2,4,6-trichloroanilino)-2,4-pyrimidinedione (50 mmol), phosphorus pentasulfide (55 mmol) and pyridine (75 ml) is heated to reflux for about 5 hours. The reaction mixture is poured into 150 ml of boiling water and allowed to cool to RT. It is then filtered, washed with water, air-dried for 10 minutes and dried in a dessicator (house vacuum) overnight to yield 5-cyano-1-(2,4,6-trichloroanilino)-4-thiopyrimidine-2-one.

EXAMPLE 11

Following the procedure of Example 1, N-(2-carbethoxyacetyl)urethane is reacted with triethyl orthoformate in acetic anhydride to give α-carbethoxy-β-ethoxy-N-ethoxycarbonylacrylamide. This is reacted with 2,4,6-trichlorophenylhydrazine, giving α-carbethoxy-β-(2,4,6-trichlorophenylhydrazino)-N-ethoxycarbonylacrylamide which is cyclized to yield 5-carbethoxy-1-(2,4,6-trichloroanilino)-2,4-pyrimidinedione.

5-Carbethoxy-1-(2,4,6-trichloroanilino)-2,4-pyrimidinedione is dissolved in a hot mixture of concentrated HCl and glacial acetic acid (1:1) and is refluxed for 10 hours. The reaction mixture is cooled to RT and filtered, giving 5-carboxy-1-(2,4,6-trichloroanilino)-2,4-pyrimidinedione.

The above acid (0.01 mol) is dissolved in 15 ml of quinoline and 0.25 g of powdered copper is added. The mixture is heated to reflux for 90 minutes under nitrogen. After cooling to RT, the mixture is poured into 50 ml of 2 N sodium hydroxide and extracted with ether (2X). The aqueous phase is acidified to pH 4–5 and is filtered to obtain 1-(2,4,6-trichloroanilino)-2,4-pyrimidinedione.

An excess of N-bromosuccinimide in acetic acid is added to 1-(2,4,6-trichloroanilino)-2,4-pyrimidinedione and the mixture is refluxed for 10 hours. It is cooled to RT and is then poured into ice and filtered to give 5-bromo-1-(2,4,6-trichloroanilino)-2,4-pyrimidinedione.

Following the above procedure, 5-chloro-1-(2,4,6-trichloroanilino)-2,4-pyrimidinedione is prepared by the reaction of 1-(2,4,6-trichloroanilino)-2,4-pyrimidinedione with an excess of chlorine in acetic acid. In place of chlorine, an excess of N-chlorosuccinimide could also be used.

EXAMPLE 12

A mixture of 1 mole of cyanoacetic acid, 1 mole of 1-(2,6-dimethylphenyl)semicarbazide and 300 ml of acetic anhydride is heated to 80° for 2 hours. The mixture is cooled to RT, 50 ml of ether is added and it is stirred at RT overnight. The reaction mixture is filtered, washed with ether (3X) and dried to give N-(2-cyanoacetyl)-1-(2,6-dimethylphenyl)semicarbazide.

One mole of the above phenylsemicarbazide is added to 400 ml of water, followed by the addition of 200 ml of ethanol. This mixture is heated to 85° and 165 ml of 10% sodium hydroxide is added. After 30 minutes the mixture is acidified to pH 5, cooled to RT, filtered and recrystallized in acetone/water, yielding 6-amino-1-(2,6-dimethylanilino)-2,4-pyrimidinedione.

To 1 mole of 6-amino-1-(2,6-dimethylanilino)-2,4-pyrimidinedione dissolved in 3 moles of dilute aqueous hydrochloric acid cooled to 0°–5° in an ice bath is slowly added 1.1 mole of sodium nitrite (dissolved in water at 5°) with rapid stirring. After addition is complete, add dropwise but rapidly 1.1 mole cuprous chloride dissolved in water. Stir for 30 minutes, then heat to 50° for 1 hour. The mixture is cooled to RT and filtered to obtain 6-chloro-1-(2,6-dimethylanilino)-2,4-pyrimidinedione.

EXAMPLE 13

Sodium nitrite (1.1 mole) dissolved in water is slowly added to a cool (0°–5°) solution of 6-amino-1-(2,6-dimethylanilino)-2,4-pyrimidinedione (1 mole) in dilute fluoboric acid. The precipitate which forms is filtered off, washed with water, dried and pyrolyzed under nitrogen (only a small amount at a time) to give 6-fluoro-1-(2,6-dimethylanilino)-2,4-pyrimidinedione.

EXAMPLE 14

To 1.35 mmol of 5-bromo-1-(2-methylanilino)-2,4-pyrimidinedione in 5 ml of 50% aqueous ethanol is added 1.41 mmol of sodium cyanide. The mixture is heated to reflux for 4 hours, after which it is cooled to RT, filtered and recrystallized from ethanol to give 6-cyano-1-(2-methylanilino)-2,4-pyrimidinedione.

5-Bromo-1-(2-methylanilino)-2,4-pyrimidinedione is prepared by hydrolysis and then decarboxylation of 5-carbethoxy-1-(2-methylanilino)-2,4-pyrimidinedione, followed by bromination, following the procedures of Example 11.

To obtain 5-chloro-6-cyano-1-(2-methylanilino)-2,4-pyrimidinedione, N-chlorosuccinimide is reacted with 6-cyano-1-(2-methylanilino)-2,4-pyrimidinedione, as described in Example 11.

EXAMPLE 15

To a mixture of 6-cyano-1-(2,6-dimethylanilino)-2,4-pyrimidinedione (50 mmol) and aqueous sodium hydroxide (50 mmol) is added 55 mmol of trichloromethylsulfenyl chloride in methylene chloride at 5° and with rapid stirring. When the pH of the mixture is 7–8, the reaction is complete. The layers are separated and the aqueous phase is discarded. The methylene chloride is removed, followed by washing with water and drying to yield a mixture of two crude products. Separation by chromatography on silica gel, eluting with acetone/hexane, gives the two final products, 6-cyano-1-(2,6-dimethylanilino)-3-trichloromethylthio-2,4-pyrimidinedione and 6-cyano-1-(2,6-dimethyl-N-trichloromethylthioanilino)-2,4-pyrimidinedione.

In the same manner as above, 6-cyano-1-(2,4,6-trichloroanilino)-2,4-pyrimidinedione in aqueous sodium hydroxide is reacted with ethylsulfenyl chloride in methylene chloride, followed by chromatography yields the compounds 6-cyano-3-ethylthio-(2,4,6-trichloroanilino)-2,4-pyrimidinedione and 6-cyano-1-(N-ethylthio-2,4,6-trichloroanilino)-2,4-pyrimidinedione.

EXAMPLE 16

Following the methods of Example 1, each of the compounds 3-chloro-2-methylphenylhydrazine, 4-fluorophenylhydrazine, 3-methoxyphenylhydrazine, 2-acetylphenylhydrazine, 4-methoxy-2-methylphenylhydrazine, 2-trifluoromethylphenylhydrazine and 3-methylphenylhydrazine is reacted with α-cyano-β-ethoxy-N-ethoxycarbonylacrylamide and the resulting product is cyclized to give 5-cyano-1-(3-chloro-2-methylanilino)-2,4-pyrimidinedione 5-cyano-1-(4-fluoroanilino)-2,4-pyrimidinedione 5-cyano-1-(3-methoxyanilino)-2,4-pyrimidinedione 5-cyano-1-(2-acetylanilino)-2,4-pyrimidinedione 5-cyano-1-(4-methoxy-2-methylanilino)-2,4-pyrimidinedione 5-cyano-1-(2-trifluoromethylanilino)-2,4-pyrimidinedione 5-cyano-1-(3-methylanilino)-2,4-pyrimidinedione.

What is claimed is:

1. A compound of the following formula:

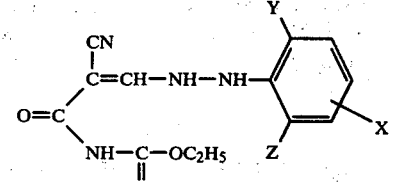

wherein each of X, Y and Z is independently selected from methyl, methoxy, chloro, fluoro, trifluoromethyl and methylthio.

2. The compound according to claim 1 wherein each of X, Y and Z is chloro and X is in the 4 position.

* * * * *